United States Patent [19]

Adcock

[11] Patent Number: 4,855,112
[45] Date of Patent: Aug. 8, 1989

[54] HIGH EFFICIENCY APPARATUS FOR AEROSOL DIRECT FLUORINATION

[75] Inventor: James L. Adcock, Knoxville, Tenn.

[73] Assignee: The University of Tennessee Research Corporation, Knoxville, Tenn.

[21] Appl. No.: 88,158

[22] Filed: Aug. 21, 1987

[51] Int. Cl.$^4$ .......................... B01J 19/08; B01J 19/26
[52] U.S. Cl. ........................... 422/186.23; 422/186.25; 422/189; 252/305
[58] Field of Search ............... 422/129, 139, 158, 162, 422/186.23, 186.25, 213, 216, 189; 252/305

[56] References Cited

U.S. PATENT DOCUMENTS

| | | | |
|---|---|---|---|
| 3,808,147 | 4/1974 | Dymet et al. | 252/305 |
| 4,113,435 | 9/1978 | Lagow | 422/91 |
| 4,281,119 | 7/1981 | Lagow | 544/106 |
| 4,330,465 | 5/1982 | Adcock | 549/380 |
| 4,377,715 | 3/1983 | Nychka et al. | 570/123 |
| 4,636,364 | 1/1987 | Geyer et al. | 252/305 |

OTHER PUBLICATIONS

"Aerosol Direct Fluorination: A Developing Synthesis Technology and an Entry Level Mechanistic Tool", A Short Review, Authors: James L. Adcock and Myron L. Cherry, Publication: Industrial & Engineering Chemistry Research, 1987, 26,208.

*Primary Examiner*—Benoît Castel
*Attorney, Agent, or Firm*—Luedeka, Hodges & Neely

[57] ABSTRACT

An apparatus for aerosol direct fluorination is disclosed in which a material to be fluorinated is formed into an aerosol prior to fluorination by introducing a vapor stream of the material to be fluorinated centrally into converging flows of carrier particles suspended in a gas and condensing the vapor onto the particles. Fluorine is contacted with the aerosol in an elongated fluorination reactor having microporous walls providing a substantially continuous influx of fluorine-containing gas which creates an increasing fluorine concentration gradient as the aerosol moves through the reactor and provides a barrier to prevent contact of the aerosol with the microporous walls. A photochemical stage includes an elliptical reflector with a light source of one focus and a flow of aerosol and fluorine at the others.

10 Claims, 2 Drawing Sheets

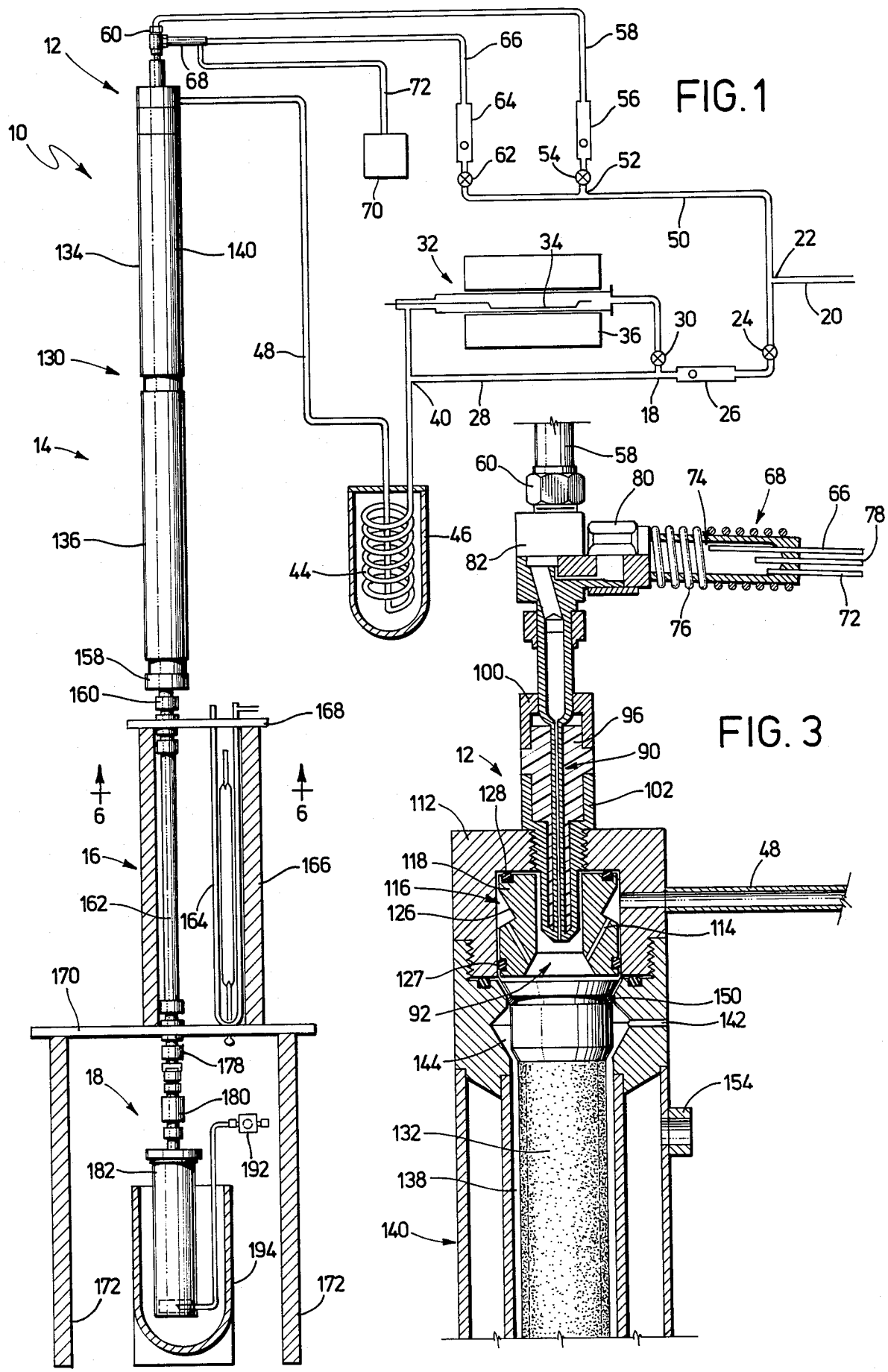

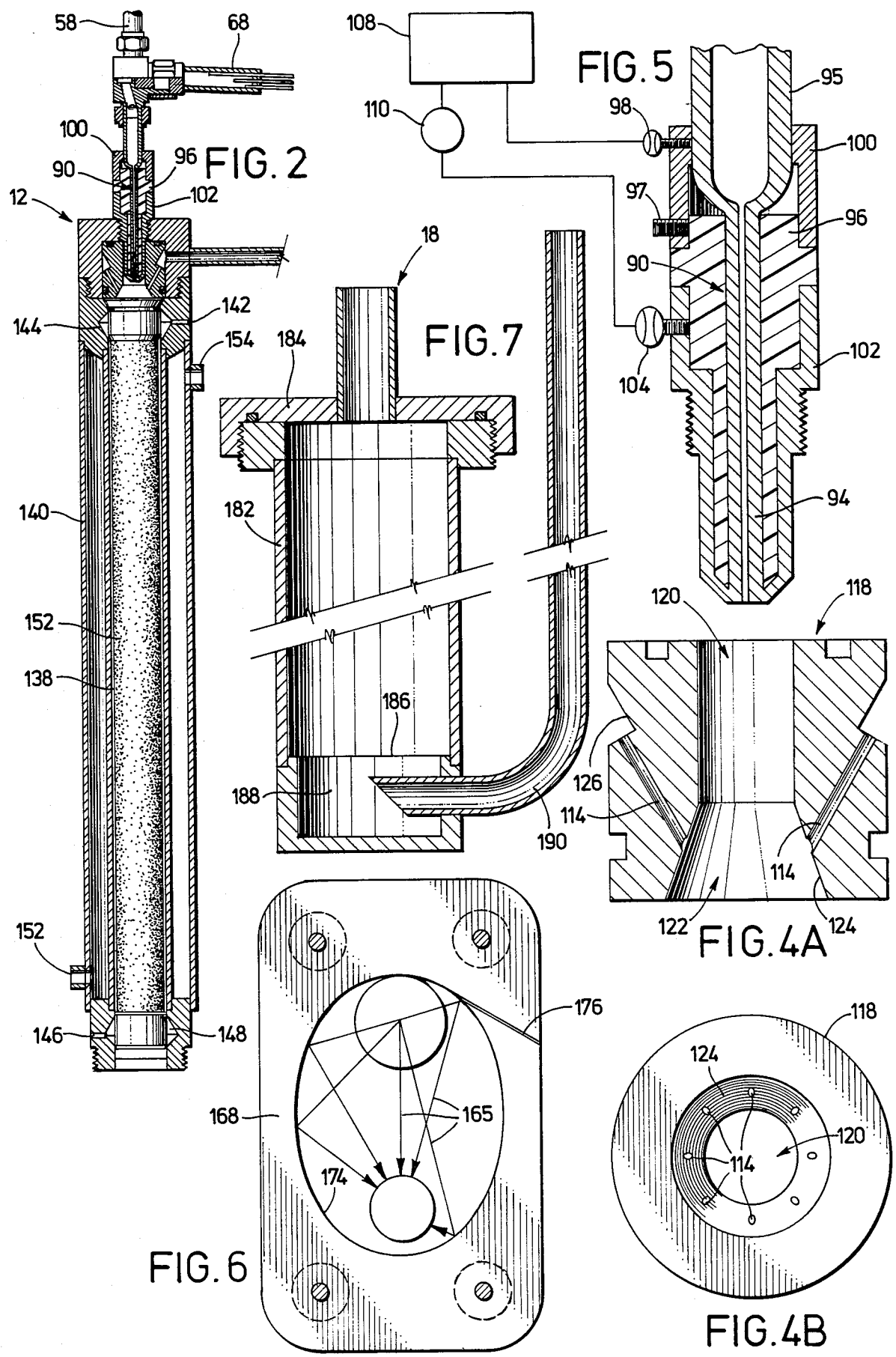

HIGH EFFICIENCY APPARATUS FOR AEROSOL DIRECT FLUORINATION

FIELD OF THE INVENTION

The present invention relates to direct fluorination and more particularly relates to an apparatus for aerosol direct fluorination which produces high yields of fluorinated products.

BACKGROUND OF THE INVENTION

Fluorinated compounds and compositions are widely used as lubricants, solvents, plasticisers, waxes, refrigerants, and as monomers for polymer production. While it is theoretically possible to efficiently produce many useful fluorinated materials by direct fluorination, most fluorinated materials are produced by indirect processes which circumvent the use of elemental fluorine. Because direct fluorination reactions are highly exothermic, appropriate measures must be taken to control the reaction to enable the production of the desired products in high yield.

U.S. Pat. No. 4,330,475, incorporated herein by reference, discloses an efficient and versatile direct fluorination method and apparatus. In this process, an aerosol containing the material to be fluorinated is flowed through a reaction zone where it is contacted with elemental fluorine under conditions such that fluorination occurs. While this process for direct fluorination enables good control of the stoichiometry to produce a desired product mix, there are some practical difficulties encountered in adjusting the quantities of reactants entering the fluorination reactor and product yields are often less than optimum.

It is accordingly an object of the invention to provide an improved aerosol direct fluorination apparatus.

It is a further object to provide an aerosol direct fluorination apparatus particularly well-suited for materials which can be vaporized and which is amenable to easy adjustment of the quantities of reactants.

It is another object to provide an aerosol direct fluorination apparatus which has the capability for high product yields.

SUMMARY OF THE INVENTION

In accordance with one form of the invention there is provided an apparatus for direct fluorination in which a material to be fluorinated is formed into a flowing aerosol prior to fluorination with elemental fluorine in a fluorination zone by introducing a gas stream containing vapor of the material to be fluorinated centrally into converging flows of carrier particles suspended in a gas in an aerosol formation zone and condensing the vapor onto the particles. In the preferred apparatus, the converging flows of suspended carrier particles have a radially-symmetric flow distribution pattern about the vapor-containing stream provided by a plurality of generally equally spaced-apart inlets in a circular arrangement which direct streams of carrier particles suspended in a gas towards a convergence region at which the vapor of the material to be fluorinated is introduced into the suspended particles and gas. In the preferred apparatus, the flowing aerosol produced in the aerosol formation zone is aligned with the original direction of the vapor-containing stream and flows directly into the reaction zone without substantial change of direction.

Further advantage is obtained in accordance with the present invention by contacting a flowing aerosol of the material to be fluorinated with fluorine in a fluorination reactor having microporous walls providing a substantially continuous influx of a fluorine-containing gas which creates an increasing fluorine concentration gradient as the flow of aerosol moves through the reactor and provides a barrier to prevent contact of the aerosol with the porous walls.

Also in accordance with the invention, a photochemical fluorination reactor is provided which employs a reflector having elliptical walls and with an elongated light source at one focus and a light-admitting reactor tube providing a generally straight-through pathway for a flow of the aerosol. The reactor tube is positioned at the other focus of the ellipse so that light produced by the light source is directed into the reactor tube.

The objects and advantages of the present invention may be appreciated and more fully understood by reference to the following detailed description and accompanying drawings in which:

BRIEF DESCRIPTION OF THE DRAWINGS

FIG. 1 is a partially schematic elevational view of a preferred embodiment of apparatus in accordance with the present invention;

FIG. 2 is a cross-sectional view of the aerosol generator and an upper reaction module of the apparatus of FIG. 1;

FIG. 3 is an enlarged view of the upper portion of the apparatus of FIG. 1;

FIGS. 4A and 4B are cross-sectional and plan views, respectively, of an aerosol generator insert employed in the apparatus of FIGS. 1, 2, and 3;

FIG. 5 is a partially schematic cross-sectional view of a heated hydrocarbon inlet conduit employed in the apparatus of FIG. 1;

FIG. 6 is a plan view of an upper support plate of the photochemical state in accordance with the present invention; and FIG. 7 is a cross-sectional view of a product trap employed in the apparatus depicted in FIG. 1.

DESCRIPTION OF A PREFERRED EMBODIMENT

Referring now to the drawings in which like reference characters designate like of corresponding parts, there shown in FIG. 1 a preferred embodiment of aerosol fluorination apparatus 10 employing various features in accordance with the present invention. Apparatus 10 includes an aerosol generator 12 which provides an "aerosol" of the material to be fluorinated. "Aerosol" as used in this patent application is intended to refer to any gaseous suspension of liquid, solid, liquid-coated solid or other such particles which remain suspended in the fluorination process as will be described. The aerosol is carried into the fluorination reactor 14 and contacted with elemental fluorine to achieve fluorination. The fluorination reactor includes stages as will be described including a photochemical stage 16. A product trap 18 is also provided for collecting the aerosol which contains products of the fluorination reaction.

The preferred aerosol generator 12 depicted in the drawings is adapted for producing aerosols of materials which can be liquified and subsequently vaporized. It will be understood that there is no intent to limit various other features of the apparatus of the invention for the fluorinationation of materials of this type.

The aerosol generator 12 depicted supplies small "pre-aerosol" particles of sodium fluoride which serve as carrier particles for forming the aerosol carried in an inert gas such as helium to an aerosol formation zone at which a vapor of the material is condensed onto the particles. With reference as to FIG. 1, helium is supplied to tubing 20 and is divided at tee 22 into two portions. The first portion flows through control valve 24 to flowmeter 26 and is again divided into two portions at tee 18. Some of the helium flows through valve 30 into furnace 32. Furnace 32 contains a nickel boat 34 containing solid sodium fluoride which is heated to between about 500° C. to about 1300° C. by tubular heaters 36. Sodium fluoride in the boat 34 sublimes into sodium fluoride particles of average radius of about 17.5 Å in the helium carrier gas stream under such conditions as described by Espenschied et al, J. Phys. Chem. 68:2321 (1964). The helium containing the sodium fluoride particles is combined at mixing tee 40 with the second portion of the helium flowing in line 28 which extends from tee 18. In general, only a portion of the helium entering tee 18 is directed into the furnace 32 to avoid excessive cooling. The combined stream from the mixing tee 40 flows into a coil 44 located in dewar 46 containing cryogenic cooling liquid such as liquid nitrogen. The stream of helium and suspended sodium fluoride particles is cooled in the preferred apparatus to near −196° C. The chilled helium suspension of sodium fluoride exits from dewar 46 in tubing 48 and enters aerosol generator 12 which will be described in more detail hereinafter.

The other portion of helium gas split at tee 22 flows in line 50 to tee 52. A portion of helium is supplied through valve 54 to flowmeter 56 and to line 58 which supplies helium to a fitting 60 on the top of the aerosol generator 12. Line 50 continues to valve 62 and flowmeter 64 which supply helium through line 66 to hydrocarbon evaporator 68. Hydrocarbon evaporator 68 is supplied with hydrocarbon in liquid form by metering pump 70 through line 72. It will be understood that the hydrocarbon to be fluorinated can be supplied by pump 70 as a liquid or can be dissolved in a solvent for the purposes of handling and metering the material. The solvent if employed is advantageously inert during the fluorination process or is reactive but produces a side product which is easily separable from desired products and does not otherwise interfere with the reaction.

Referring now to FIG. 3 which shows the aerosol generator 12 in enlarged cross-section, hydrocarbon supply line 72 and helium line 66 enter a hydrocarbon evaporation chamber 74. In the chamber, a coiled heating element 76 around chamber 74 vaporizes the supplied liquid hydrocarbon (and solvent if present) and a low volume (50–100 cc/s) of helium entering through line 66 mixes with the vapor and carries the vapor from the chamber 74. A thermocouple 78 is provided in the chamber 74 to monitor temperature. The vapor and helium is filtered by filter 80 to remove nonvaporized materials before joining at mixer 82 the primary helium flow entering the aerosol generator 12 through line 58.

In order for the helium-hydrocarbon mixture to be carried into the aerosol generator 12 without the hydrocarbon condensing on the aerosol generator components, a heated hydrocarbon conduit 90 is provided which supplies the hydrocarbon to the aerosol formation zone 92 within the aerosol generator 12. As illustrated most clearly in FIG. 5, the heated conduit 90 is provided by a thin wall tube 94 which is heated electrically. In the preferred embodiment illustrated, the electrical resistance of the thin wall tube 94 itself is employed for heating and a suitable tube is a ⅛ inch stainless steel tube with a 0.012 inch wall thickness. This is accomplished by mounting the thin wall tube 94, which has a thick-walled upper region 95, within an electrical insulator such as teflon insulator 96 depicted. An upper cap 100 is fitted over the upper portion of the insulator 96 and has an opening for receiving the thick-walled portion 95 of the tube 94. The upper cap is attached to the insulator by three set screws 97 (one being shown) and is electrically connected to the tube by contact screw 98. A lower cap 102 provides for threadable connection to the aerosol generator 12 as will be described. The lower cap also provides an electrical connection to the lowermost portion of the thin wall tube 94. To heat the conduit all the way to the opening into the conduit to avoid hydrocarbon condensation, the lower cap 102 is elongated and is attached adjacent the opening of the thin wall tube 94 such as by welding or silver soldering. The upper cap 100 and lower cap 102 are insulated from each other by insulator 96 constructed such that the thin wall tube 94 provides the only electrical connection and has the most resistance to the flow of electric current when a voltage is supplied between the upper cap 100 and the lower cap 102 through contact screw 98 and contact screw 104, respectively. A voltage source 108 and rheostat 110 provide an adjustable voltage between the upper and lower caps to heat the conduit 90 as desired.

Referring again to FIG. 3, the suspended "pre-aerosol" sodium fluoride particles are supplied to the aerosol formation zone 92 at which the vaporized hydrocarbon condenses on the particles to form the aerosol. The hydrocarbon vapor stream is directed centrally into converging flows of gases containing the sodium fluoride pre-aerosol particles. In the preferred embodiment, this is accomplished by providing a plurality of spaced-apart streams in a circular arrangement which converge as the vapor is introduced to the suspended particles. It is preferable for the sodium fluoride and helium entering the aerosol formation zone to be sufficiently cold that the vapor condenses as an ice on the particles to prevent the aerosol particles from having a "sticky" surface although liquid-coated aerosol particles are acceptable for some applications. A common temperature for the helium and suspended particles entering the aerosol formation zone is between about −150° C. and about −200° C., the requirement being that the temperature of the combined gases is at or below the coalescence temperature of the vapor.

The preferred aerosol generator 12 includes an upper housing cap 112 which provides a cylindrical interior area. The cap 112 also threadably receives and supports the heated hydrocarbon conduit 90 in a vertical orientation. Tubing 48 supplies suspended sodium fluoride particles into the interior of housing cap 112 from the side as shown in FIG. 3 which is supplied to a plurality of pre-aerosol inlets 114 which provide converging streams as will be described.

Referring still to FIG. 3 and also to FIGS. 4A and 4B, the preferred apparatus employs an aerosol generator insert 118 within cap 112 to provide the pre-aerosol inlets 114. The aerosol generator insert 118 has an overall cylindrical configuration and is fabricated from a suitable material such as teflon. As shown most clearly in FIGS. 4A and 4B, the aerosol generator insert 118 includes a cylindrical throat 120 which receives the heated hydrocarbon conduit 90 when fitted within the cylindrical interior area of the cap 112. Below the throat 120, the insert provides an expanding region 122 in which the diameter of the throat expands towards the lowermost portion of the insert to achieve an opening about one inch in diameter. The expanding region 122 thus provides a generally frustro-conical wall 124 having an angle with respect to its axis such that a smooth transition to the diameter of the fluorination zone is achieved and in which the pre-aerosol inlets 114 are provided.

In the preferred embodiment, eight pre-aerosol inlets 114 are arranged in an equally spaced-apart circular arrangement with a diameter of about 0.80 inch about the axis of the throat 120. The inlets 114 are angled towards each other so that the suspended particle streams emitted from the inlets converge at a generally common location. A convergence angle of about 30° with respect to the axis of the throat has been found to be suitable. The inlets 114 provide discrete streams which enter the throat 120. The inlets 114 are suitably provided by bores in the insert having a diameter of about 0.060 inch and having a length of between about 0.5–1 inch.

Referring again to FIG. 3, the aerosol generator insert 118 together with the upper housing cap 112 provide a manifold area 116 for the helium and suspended particles. An annular groove 126 provided on the exterior of the aerosol generator insert 118 receives the suspended sodium fluoride particles from line 4 and distributes the suspended material to the pre-aerosol inlets 114 in the insert 118. In order to prevent leakage around the insert in the upper housing cap 112, a lower O-ring 127 is provided within a suitable groove in the side wall of the aerosol generator insert 118. An upper O-ring 128 is similarly provided in the upper surface of the insert 118 to provide a seal to the interior of the housing cap 112.

Referring to FIGS. 1, 2 and 3, the aerosol produced by the aerosol generator 12 flows into a subambient temperature stage 130 of the fluorination reactor 14 which provides a vertically elongated reaction zone. Preferably, the vertically elongated reaction zone is generally cylindrical in configuration and has an axis which is generally aligned with the heated conduit 90 which provides the vapor stream in the aerosol generator. The aerosol generator 12 thus flows into the fluorination reactor without any substantial change in flow direction. The subambient stage provides a fluorine concentration gradient wherein the aerosol particles being carried downwardly through the reactor 14 encounter progressively higher fluorine concentrations and higher temperatures. The subambient temperature stage 130 is preferably provided by reactor modules having microporous elements 132 for allowing a fluorine containing gas, e.g., helium-fluorine mixtures, to gradually and continuously flow into the aerosol. The microporous elements have an extremely large number of small pores which provide an influx of fluorine-containing gas such that a generally uniform barrier layer of gas along the inside wall of the porous elements substantially prevents contact of the aerosol particles with the walls. As shown in FIG. 1, the subambient temperature stage 130 is comprised of first and second modules 134 and 136, respectively, with first and second modules being essentially identical in construction and thus only the module 134 will be described in detail. A fewer or greater number of interconnected modules can be employed to achieve the desired reaction conditions.

First module 134 includes a porous element 132 which defines an elongated, generally vertical cylindrical flow path through the reactor. A monel element with 2 micron porosity has been found to be a suitable microporous element which provides an influx of fluorine-containing gas which is substantially continuous and without large or directed streams which interfere with the formation of a barrier layer of gas to prevent contact of aerosol with the walls. The diameter of the flow path in the preferred embodiment is about 1 inch and the element 132 has a length of about 20 inches. The porous monel element 132 is supported in the reactor 14 by jacket 140 which is threadably connected to the upper housing cap 112 and, at its lower most end, is threadably connected to a like jacket 140 of the second module 136 to connect the modules together so that the porous element 132 of the second module provides a substantially continuous flow path of increased length.

The jacket 140 is constructed such that there is a generally uniform fluorine flow space 138 between the exterior of the porous monel element and the inside of the jacket 140. In the upper portion of the jacket 140, there is a fluorine-containing gas inlet 142 which supplies fluorine-helium mixtures to an annular space 144 which is in fluid communication with the fluorine flow space 138. A lower fluorine-containing gas inlet and annular space 146 and 148, respectively, are similarly provided at the lower end of the jacket 140. Appropriate supply tubing, valves, and flowmeters (not shown) are employed to provide helium-fluorine mixtures to the inlets 142 and 146. A fluorine-helium mixture supplied through the inlets 142 and 146 is distributed to the space 138 between the element 132 and the inside of the jacket 140 so that fluorine is supplied into the interior of the reactor by flowing through the element 132. As shown for the upper end of element 132 in FIG. 3, O-ring 150 and appropriate annulrr groove are provided in the upper and lower nonporous ends of the monel element 132 to confine the flow of the fluorine-helium mixture to the annular spaces 144 and 148 and the flow space 138 between the jacket 140 and the element 132.

In the preferred embodiment depicted, the fluorine flow space 138 is sufficiently small that a pressure drop occurs as the fluorine-containing gas flows through the space 138 away from each of the annular spaces 144 and 148. This enables control over the fluorine concentration gradient established in the module 134. Generally, the lower inlet 146 is employed to establish the maximum fluorine influx at the lower end of the module 134 and the influx through the walls tapers off gradually upwardly from the inlet 146. The upper inlet 142 establishes the initial fluorine concentration encountered by the aerosol and the influx tapers off as the aerosol flows downwardly. The additive effects of supplying fluorine through both inlets provides a concentration gradient which can be adjusted as desired.

Jacket 140 provides subambient temperature cooling for the reaction occurring within the porous elements 132. In the preferred apparatus 10 depicted, the jacket 140 provides a double-walled construction with the inner wall defining the fluorine flow space 138 surrounding the porous monel element 132. Within the double walls of the jacket 140 a heat transfer fluid is circulated which has a boiling/freezing point compatible with the reaction conditions being employed. A suitable fluid is sold under the trademark FREON 11. As shown most clearly in FIG. 2, a heat transfer fluid inlet 152 is provided in the lower area of the jacket 140 and a heat transfer fluid outlet 154 is provided in the upper portion of the jacket 140 so that the heat transfer fluid flows in the jacket 140 generally oppositely to the flow of reactants within the reactor. Suitable temperature sensors (not shown) are provided to monitor the temperature within the reactor 14 so that the temperature and circulation rate of the heat transfer fluid can be appropriately adjusted.

Referring now to FIG. 1 and FIG. 6, the construction and operation of the photochemical stage 16 may be understood. Typically, molecules leaving the subambient temperature stage 130 of the reactor 14 are forty percent to sixty percent fluorinated. It is believed that the photochemical reactor completes the fluorination by removing very unreactive residual hydrogen from the molecules by dissociating molecular fluorine and directly or indirectly producing activated hydrylfluorocarbon molecules which scavenge available molecular fluorine. This results in virtually one hundred percent perfluorination with minimal fragmentation of the carbon skeletons. The photochemical stage thus avoids the great stoichiometric excesses and/or long reaction times which would be required otherwise for perfluorination.

In accordance with the present invention, the photochemical stage 16 has a straight-through design so that the reactants flowing generally vertically downwardly from the subambient temperature stage 130 enter and flow through the photochemical stage 16 without any substantial change of direction. A suitable end cap 158 is threadably secured to the jacket 140 on the lower end of the second module 136 and appropriate fittings 160 are provided to connect the end cap 158 to the photochemical reactor 156. The reactor 16 includes an elongate quartz tube 162 with an outside diameter of about 1 inch and is lined inside with 10 mil perfluorinated ethylene propylene copolymer sheeting such as that available under the trademark TEFLON FEP from DuPont which protects the quartz tube from hydrogen fluoride attack. The quartz tube 162 confines the flowing reactants and admits light produced by a water-cooled mercury arc lamp 164. In order to maximize the amount of light directed into the quartz tube 162, a reflector 166 having an interior wall which is elliptical in horizontal cross-section is provided as may be understood most easily from FIG. 6. (The front portion of the reflector is shown removed in FIG. 1.) The glass tube 162 and the mercury arc lamp 164 are provided in a generally parallel side-by-side relationship with the mercury arc lamp 164 being at one focus of the ellipse and the center of the glass tube 162 being at the other focus of the ellipse. In general, light produced by the mercury arc lamp 164 and represented in FIG. 6 by arrows 165, regardless of direction, is reflected off of the walls of the reflector 166 and into the glass tube 162.

In the preferred embodiment depicted, the reflector 166, the glass tube 162 and mercury arc lamp 164 are supported by a top plate 168 and a bottom plate 170 which are interconnected by generally vertical pillars (not shown). The top plate and bottom plate 168 and 170 are provided with suitable openings for receiving fittings which support the glass tube 162 and mercury arc lamp 164. In the preferred embodiment, the reflector 166 is provided by a polished, thin metal plate such as aluminum having a thickness of about 0.020 inches.

Referring to FIG. 6, the top plate 168 has a downwardly facing groove 174 defining an ellipse about the glass tube 162 and mercury arc lamp 164 and the bottom plate 170 has a corresponding upwardly extending groove (not shown) similar to the groove in the top plate 168. The top and bottom plates 168 and 170 thus support the reflector 166 in an elliptical configuration by holding it within the grooves in the top and bottom plates. To facilitate assembly of the photochemical reactor 156, a tangential assembly groove 176 is provided in both the top plate 168 and the bottom plate 170 to permit the reflector 166 to be inserted without disassembly of the apparatus. As shown in FIG. 6, the assembly groove 176 is a generally linear groove extending from the edge of top plate 168 and extends tangentially to the elliptical groove 174. A similar assembly groove is provided in the bottom plate 170 directly below the groove 176 in the top plate 168. The assembly groove 176 thus enables the reflector 166 to be slid into the grooves and between the plates for assembly of the photochemical reactor. Bottom plate 170 is supported on pillars 172 which aid in supporting the entire apparatus 10.

Referring now to FIGS. 1 and 7, the preferred product trap 18 is depicted. Product trap 18 is positioned beneath bottom plate and includes appropriate connection fittings 176 and valve 180 for control of the flow to the product trap. The product trap 18 includes vessel 182 having a diameter of several times the diameter of the reactor 14 so that the flow velocity of gases and suspended materials in the trap is much lower than in reactor 14. As illustrated in FIG. 7 for the preferred embodiment, vessel 182 includes access cap 184 which is removable for providing access into the vessel. Vessel 182 has a intermediate floor 186 comprised of a 40 micron filter disc. The intermediate floor 186 supports sodium fluoride pellets (not shown) within the vessel and provides open space 188 beneath the intermediate floor. A product trap outlet 190 extends from the open space 188 to vent gas free of the product as controlled by outlet valve 192. The vessel 182 is immersed in dewar 194 which is filled with a low temperature cooling fluid which, in the preferred embodiment, is liquid nitrogen. It is believed that the product trap 18 illustrated collects the aerosol particles on the sodium fluoride pellets by operation of the static charge which builds up on the pellets due to the flow of the gases through the product trap 18 under the conditions employed. These pellets also scrub hydrogen fluoride from the product (by forming sodium bifluoride). It will be understood that while the preferred product trap 18 provides the advantage that it is essentially self-operating, other product traps such as cyclone separators may also be used. The gas emitted from the outlet valve 192 is passed through appropriate traps (not shown) to scrub residual hydrogen fluoride and to remove residual elemental fluorine, e.g., by employing an alumina trap.

The apparatus in accordance with the invention can be used in the direct fluorination of a wide variety of materials. It is, of course, necessary when employing the preferred apparatus 10 depicted that the material to be fluorinated be capable of being vaporized. The preferred apparatus is thus most widely useful for organic compounds including straight chain or cyclic, substituted or unsubstituted, aliphatic hydrocarbon compounds and heterocyclic compounds. While aromatic or other unsaturated compounds can be fluorinated they are generally converted into a fluorinated aliphatic analogue in the fluorination process. The aerosol fluorination method and apparatus produces excellent yields of perfluorinated alkanes, esters, ketals, alkyl chlorides, acyl fluorides (from acyl fluorides and fluorides or esters), and moderate yield of perfluorinated esters and ketones, including the highly branched ketones, as well as the perfluorinated orthoesters.

Employing the apparatus 10 according to the present invention, process parameters can be varied somewhat independently. Reactor temperature gradients, residence time, stoichiometry, reactant concentrations, and flow rates can be adjusted. Being a continuous process, the reactor can be operated at a steady state with selected reaction parameters.

Temperature in the early stages of the reaction are desirably kept low, e.g. −78° C. to 0° C., and are increased towards ambient temperatures as the materials become partially fluorinated and acquire a resistance to further attack by fluorine. Similarly, the apparatus 10 with two inlets in each module enables the fluorine concentration to gradually increase since along the entire length of the subambient stage 130 of the reactor. In a typical reaction, the fluorine concentration reaches two percent to five percent by volume which is generally about twice the stoichiometrically required quantity. Typically, a particle requires from about 0.5 to about 1.5 minutes to traverse the reactor.

The aerosol generator 12 employed in the present invention efficiently produces an aerosol of the material to be fluorinated since the hydrocarbon is directed centrally into a converging flow of carrier particles and gas and thus the system is inherently "focused." This configuration of the aerosol generator provides for ease of adjustment of the quantities of reactants, gas flow rates, and the nature of the aerosol being formed. Good aerosols are produced within a wide range of throughputs of materials to be fluorinated. In the preferred embodiment, the alignment of the fluorination reactor including the photochemical stage with the flow of aerosol from the aerosol generator 12 provide efficient input of aerosol into the reactor and minimizes aerosol loss.

The subambient stage 130 provides a continuous fluorine concentration gradient and temperature gradient as is necessary for efficient fluorination. Since the influx of fluorine-containing gas is continuous and surrounds the flowing aerosol, a barrier layer is established along the walls of the porous element 132 which prevents product loss and fowling due to contact with the reactor walls.

The photochemical stage in accordance with the invention provides efficient use of the supplied light and, being of straight-through design, limits the build-up of product on the walls of the quartz tube 162.

The method and apparatus of the invention is capable of achieving direct perfluorination of a wide variety of compounds including C14 or greater hydrocarbon compounds in good yield with short reaction times.

The invention is further illustrated by the following examples.

EXAMPLE 1

Aerosol Fluorination of Pentaethylene Glycol Dimethyl Ether

The aerosol fluorination of 6.8 grams (25.6 mmoles) of pentaglyme is carried out employing the preferred reactor illustrated, and after a 4.5 hour reaction time 8.5 grams of crude product is collected. Details of the fluorination parameters are given in Table I. One hour after the reaction is complete the product trap is evacuated and the product is transferred to the vacuum line. The trap is then pumped upon with a five micron vacuum for a period of 24 hours to insure complete removal of all products. The product is then vacuum fractionated through −45° C., −78° C., −131° C., and −196° C. cold traps. When fractionation is complete, 5.78 grams remain at −45° C., 0.84 grams at −78° C., and 1.88 grams at −196° C. There is no visible product in −131° C. cold trap.

Infrared analysis shows totally perfluorinated products in all traps with the desired product in the −45° C. and −78° C. traps. The separation of the product is carried out on preparative gas chromatography SE-52 column at 25° C. then raised 2° per minute until all peaks are eluted from the column. The detector and injector temperatures are set at 180° C. and 120° C. respectively. Gas chromatographic separation of the −45° C. trap gives one major peak, retention time 28 min with 98 percent of the total peak area. $^{19}F$ nmr analysis of the peak proves it to be F-pentaethylene glycol dimethyl ether. Column separation of the −78° C. fraction gives three peaks with retention time 11.0 minutes, 21.2 minutes, 30.2 minutes with 6.0 percent, 11.0 percent, and 83.0 percent of the total peak area respectively. $^{19}F$ nmr shows the third peak to be F-pentaglyme.

Yield of F-pentaethylene glycol dimethyl ether based on hydrocarbon throughput is 33.8 percent with an effluent concentration of 69 percent.

TABLE I

AEROSOL FLUORINATION OF PENTAETHYLENE GLYCOL DIMETHYL ETHER

| Parameters | Example 1 |
|---|---|
| Fluorine flows (cc/min) | |
| Module 1-top | 20.0 |
| Module 1-bottom | 62.0 |
| Module 2-top | 62.0 |
| Module 2-bottom | 0.0 |
| Helium diluent (cc/min) | |
| Module 1-top | 170.0 |
| Module 1-bottom | 170.0 |
| Module 2-top | 170.0 |
| Module 2-bottom | 170.0 |
| Reactor Temperature (°C.) | |
| Module 1 | −20.0 |
| Module 2 | −10.0 |
| Main Carrier Helium (cc/min) | 500.0 |
| Evaporator/Sublimator Temperature (°C.) | 335.0 |
| Evaporator/Sublimator Helium Flow (cc/min) | 30.0 |
| Sodium Fluoride Particulate Furnace Helium Flow (cc/min) | 500.0 |
| Hydrocarbon Throughput (mmol/hr) | 7.1 |
| Reaction Time (hour) | 4.5 |
| Product[a] Distribution, % Collected | 69.0 |
| Product Yield (grams) | 5.4 |
| Product Yield, % Theoretical | 33.8 |

[a] F-pentaethylene glycol dimethyl ether

EXAMPLE 2

Aerosol Fluorination of Hexaethylene Glycol Dimethyl Ether

The aerosol fluorination of 6.22 grams of hexaglyme is carried out on the reactor illustrated, and after a five hour reaction time 4.08 grams of crude product is collected. Details of the fluorination are given in Table II. One hour after the reaction is complete, the product trap is evacuated and the product is transferred to the vacuum line. The trap is then pumped upon with a five micron vacuum for a period of 24 hours to insure complete removal of all products. The product is then vacuum fractionalized through −45° C., −78° C., −131° C., and −196° C. cold traps. When the fractionation is complete 1.6 grams remain at −45° C., 1.3 grams at −78° C., <0.1 grams at −131° C., and 1.1 grams at the −196° C.

Infrared analysis shows total perfluorination of products collected in all traps. The desired product stays in the −45° C. and −78° C. traps. The separation of the contents of the −45° C. trap is performed on a preparative gas chromatography SE-52 column at 25° C. and the temperature is increased at 2° per minute until no further peaks are observed and the baseline returns to normal. The chromatograph gives only one major component with 99 percent of the total peak area. $^{19}$F nmr and infrared analysis shows the peak to contain F-Hexaethylene glycol dimethyl ether. Throughput yield of F-Hexaglyme based on hydrocarbon input is 21.4 percent with an effluent concentration of 72.5 percent.

TABLE II

| AEROSOL FLUORINATION OF HEXAETHYLENE GLYCOL DIMETHYL ETHER | |
|---|---|
| Parameters | Example 2 |
| Fluorine flows (cc/min) | |
| Module 1-top | 5.0 |
| Module 1-bottom | 25.0 |
| Module 2-top | 37.0 |
| Module 2-bottom | 20.0 |
| Helium diluent (cc/min) | |
| Module 1-top | 170.0 |
| Module 1-bottom | 170.0 |
| Module 2-top | 170.0 |
| Module 2-bottom | 170.0 |
| Reactor Temperature (°C.) | |
| Module 1 | −20.0 |
| Module 2 | −10.0 |
| Main Carrier Helium (cc/min) | 500.0 |
| Evaporator/Sublimator Temperature (°C.) | 335.0 |
| Evaporator/Sublimator Helium Flow (cc/min) | 30.0 |
| Sodium Fluoride Particulate Furnace Helium Flow (cc/min) | 500.0 |
| Hydrocarbon Throughput (mmol/hr) | 7.1 |
| Reaction Time (hour) | 6.0 |
| Product$^a$ Distribution, % Collected | 72.5 |
| Product Yield (grams) | 2.9 |
| Product Yield, % Theoretical | 21.4 |

$^a$F-hexaethylene glycol dimethyl ether

EXAMPLE 3

Aerosol Fluorination of Methyl 4-Methoxybutanoate

The aerosol fluorination of methyl 4-methoxybutanoate (6.0 grams, 45.5 mmoles) is carried out on the reactor preferred illustrated and yielded 9.1 grams (69%) of crude product after a four hour and ten minute reaction time. The crude product is transferred to a vacuum line and fractionalized through −45° C., −78° C., −131° C., and −196° C. cold traps. Infrared analysis of the 3.73 grams of product in the −45° C. trap shows the presence of the perfluorinated ester. The −78° C. trap contains 3.82 grams of a mixture with approximately 30% perfluorinated ester and 70% prefluorinated acid fluoride as estimated by infrared analysis of the carbonyl intensities. The −196° C. trap contains 0.97 grams of carbonyl fluoride which is discarded. The perfluorinated ester and acid fluoride are separated by preparative gas chromatography (QF-1 column). The QF-1 column is held at 30° for 10 minutes and then is raised 0.5° per minutes until 70° is reached. It is held at 70° C. for 5 minutes and the column is then baked off at 100° C. The gas chromatogram of the −78° C. trap consists of five peaks. It is determined that the perfluorinated acid fluoride elutes in 16 minutes and the perfluorinated methyl ester elutes in 25 minutes with 26 percent and 60 percent total peak area, respectively. The other three peaks make up only 14 percent of the total peak area and are not characterized. Details of the fluorination parameters are given in Table III. The throughput yield of the perfluorinated ester is 30.8 percent and that of the perfluorinated acid fluoride is 20.2 percent. Effluent concentrations are 53.6 percent and 29.4 percent, respectively.

TABLE III

| AEROSOL FLUORINATION OF METHYL 4-METHOXYBUTANOATE | | |
|---|---|---|
| Parameters | Example 3 | |
| Fluorine flows (cc/min) | | |
| Module 1-top | 9.5 | |
| Module 1-bottom | 28.5 | |
| Module 2-top | 39.0 | |
| Module 2-bottom | 34.0 | |
| Helium diluent (cc/min) | | |
| Module 1-top | 170.0 | |
| Module 1-bottom | 170.0 | |
| Module 2-top | 170.0 | |
| Module 2-bottom | 170.0 | |
| Reactor Temperature (°C.) | | |
| Module 1 | −10.0 | |
| Module 2 | 0.0 | |
| Main Carrier Helium (cc/min) | 500.0 | |
| Evaporator/Sublimator Temperature (°C.) | 135.0 | |
| Evaporator/Sublimator Helium Flow (cc/min) | 30.0 | |
| Sodium Fluoride Particulate Furnace Helium Flow (cc/min) | 500.0 | |
| Hydrocarbon Throughput (mmol/hr) | 11.3 | |
| Reaction Time (hour) | 4.2 | |
| Product Distribution, % Collected | 29.4$^a$ | 53.6$^b$ |
| Product Yield (grams) | 2.6$^a$ | 4.8$^b$ |
| Product Yield, % Theoretical | 20.2$^a$ | 30.8$^b$ |

$^a$F-4-methoxybutanoyl fluoride
$^b$F-methyl F-4-methoxybutanoate

While a preferred embodiment of apparatus in accordance with the invention and several examples have been included in the foregoing detailed description, there is no intent to limit the scope of the claims by such disclosure and it is contemplated that numerous changes and modifications without departing from the spirit of the invention as set forth in the appended claims.

What is claimed is:

1. A direct fluorination apparatus for fluorinating material capable of being vaporized, comprising:
   carrier particle means for providing a source of solid carrier particles suspended in a gas;
   vapor means for producing a gas containing vapor of the material to be fluorinated;
   fluorine means for providing a source of gas containing elemental fluorine;
   an aerosol generator comprising an interior space with a flow outlet, first inlet means in flow communication with said carrier particle means and configured to introduce said carrier particles suspended in a gas from said carrier particle means into said interior space in converging flow streams directed substantially toward a convergence zone, and second inlet means in flow communication with said vapor means and configured to introduce a flow of said gas containing vapor of the material from said vapor means into said interior space directed into the approximate center of said convergence zone wherein said vapor condenses onto said carrier particles to produce an aerosol comprising said carrier particles with said vapor of the material to be fluorinated condensed thereon;

a fluorination reactor comprising an elongate tubular reactor defined by an elongate cylindrical wall means defining a confined flow path space through said fluorination reactor and said cylindrical wall means being in flow communication on its exterior with said fluorine means and having inlet and outlet open ends, said inlet open end being in flow communication on with said flow outlet of said aerosol generator so that said aerosol flows into said tubular reactor from said aerosol generator and through said flow path space defined by said cylindrical wall means to said exit open end thereof, and said cylindrical wall means being configured to diffusingly admit said gas containing elemental fluorine therethrough from said fluorine means without large or directed flow streams and substantially continuously over the area of said wall means to provide substantially continuous admittance of said gas containing elemental fluorine into said flow path space along said wall means, whereby flowing said aerosol through said flow path space causes said continuously admitted gas containing elemental fluorine to be swept along said wall means and closely adjacent thereto to provide a continuous insulating layer of said gas containing elemental fluorine between said wall means and said aerosol flowing therethrough, said layer simultaneously providing elemental fluorine for reacting with said flowing aerosol to cause the material to be fluorinated, and confining said flowing aerosol interiorly of said layer and thus substantially preventing contact between said flowing aerosol and said wall means; and said fluorination reactor being configured and positioned with respect to said aerosol generator so that said convergence zone is closely adjacent to and centrally disposed relative to said layer of said gas containing fluorine such that said aerosol flowing into said flow path space defined by said cylindrical wall means is confined interiorly of said layer of gas containing elemental fluorine substantially immediately upon its formation.

2. The apparatus of claim 1 wherein said second inlet means comprises a cylindrical conduit having a flow axis and is configured to direct a stream of said gas containing vapor of the material to be fluorinated into said convergence zone and said first inlet means provides converging flow streams of said suspended particles in a gas in a generally radially symmetric flow distribution pattern with respect to said flow axis.

3. The apparatus of claim 2 wherein said second inlet means for providing a generally radially symmetric flow distribution pattern of said suspended particles in a gas comprises a plurality of inlets arranged in a circular arrangement which direct said suspended particles in a gas towards said convergence zone.

4. The apparatus of claim 3 wherein said plurality of inlets comprise eight generally evenly spaced-apart inlets.

5. The apparatus of claim 3 wherein said plurality of inlets and said cylindrical conduit are oriented so that the resulting flow aerosol is aligned with the flow axis of said cylindrical conduit.

6. The apparatus of claim 2 wherein said flow axis of said cylindrical conduit is vertical and directs a stream downwardly into said convergence zone.

7. The apparatus of claim 2 wherein said elongate cylindrical wall means of said fluorination reactor is generally aligned with said flow axis of said cylindrical conduit.

8. The apparatus of claim 1 wherein said elongate cylindrical wall means is defined by a microporous material.

9. Apparatus for fluorinating a material comprising:
aerosol generation means for producing a flowing aerosol of the material to be fluorinated;
an initial fluorination reactor in flow communication with said aerosol generation means, said initial fluorination reactor providing an initial reaction zone for receiving said flowing aerosol from said aerosol generation means, and said initial fluorination reactor being in flow communication with a source of elemental fluorine to admit said elemental fluorine therein and contact said aerosol with the elemental fluorine under conditions such that fluorination occurs to at least partially fluorinate said material; and
a photochemical reactor in flow communication with said initial fluorination reactor to receive a flow of said at least partially fluorinated material therein for further fluorinating said at least partially fluorinated material, said photochemical reactor comprising a transparent tube having a tube axis for receiving and conveying said partially fluorinated material and fluorine through the photochemical reactor along a substantially straight-through pathway, an elongated light source with a light source axis and means supporting said light source adjacent said transparent tube in a side-by-side relationship therewith so that said light source axis is generally parallel to said transparent tube, and a reflector with means supporting said reflector adjacent said transparent tube and said reflector having internal reflecting walls with an elliptical cross-section in a plane perpendicular to the tube axis and light source axis, said tube axis being at one focus of the ellipse and said light source axis being at the other axis of the ellipse whereby light produced by said light source is reflected into said transparent tube.

10. The apparatus of claim 9 wherein said initial fluorination reactor provides a generally cylindrical, vertically oriented initial reaction zone about an initial reaction zone axis above said photochemical reactor, said aerosol flowing downwardly through said initial reaction zone into said photochemical reaction zone, said initial reaction zone axis being generally aligned with said tube axis whereby said flowing aerosol does not substantially change flow direction upon entering said photochemical reaction zone.

* * * * *

UNITED STATES PATENT AND TRADEMARK OFFICE
CERTIFICATE OF CORRECTION

PATENT NO. : 4,855,112

DATED : August 8, 1989

INVENTOR(S) : James L. Adcock

It is certified that error appears in the above-identified patent and that said Letters Patent is hereby corrected as shown below:

Column 5, line 31 "4" should be --48--

Column 6, line 39 "annulrr" should be --annular--

Column 11, line 2 "fractionalized" should be --fractionated--

Column 11, line 55 "fractionalized" should be --fractionated--

Column 13, line 16 after communication, delete "on"

Signed and Sealed this

Seventh Day of August, 1990

Attest:

HARRY F. MANBECK, JR.

Attesting Officer

Commissioner of Patents and Trademarks